United States Patent [19]

Rambach

[11] Patent Number: 5,962,251
[45] Date of Patent: *Oct. 5, 1999

[54] METHOD FOR THE IDENTIFICATION OF MICROORGANISMS WITH AT LEAST TWO CHROMOGENS

[76] Inventor: Alain Rambach, 73 boulevard Montparnasse 75006, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/591,611

[22] PCT Filed: Jul. 28, 1994

[86] PCT No.: PCT/FR94/00958

§ 371 Date: Jan. 26, 1996

§ 102(e) Date: Jan. 26, 1996

[87] PCT Pub. No.: WO95/04157

PCT Pub. Date: Feb. 9, 1995

[30] Foreign Application Priority Data

Jul. 28, 1993 [FR] France ................................ 93 09294

[51] Int. Cl.⁶ ...................................................... C12Q 1/04
[52] U.S. Cl. ................................................. 435/34; 435/29
[58] Field of Search ................................ 435/4, 7.2, 29, 435/30, 34

[56] References Cited

U.S. PATENT DOCUMENTS

| | | |
|---|---|---|
| 4,874,695 | 10/1989 | Pincus ........................................ 435/19 |
| 5,089,395 | 2/1992 | Snyder et al. ............................. 435/39 |
| 5,210,022 | 5/1993 | Roth et al. ................................ 435/34 |
| 5,358,854 | 10/1994 | Ferguson ................................... 435/14 |
| 5,364,767 | 11/1994 | Flowers et al. ........................... 435/39 |
| 5,393,662 | 2/1995 | Roth et al. ................................ 435/38 |
| 5,449,612 | 9/1995 | Lepargneur et al. ..................... 435/18 |
| 5,464,755 | 11/1995 | Bochner .................................... 435/34 |
| 5,510,243 | 4/1996 | Boyd et al. ............................... 435/18 |
| 5,534,415 | 7/1996 | Orenga ..................................... 435/34 |
| 5,716,799 | 2/1998 | Rambach .................................. 435/34 |

FOREIGN PATENT DOCUMENTS

| | | |
|---|---|---|
| 0065137 | 11/1982 | European Pat. Off. . |
| 0451775 | 10/1991 | European Pat. Off. . |
| 8605206 | 9/1986 | WIPO . |

*Primary Examiner*—José G. Dees
*Assistant Examiner*—Dameron Jones
*Attorney, Agent, or Firm*—Blakely, Sokoloff, Taylor & Zafman

[57] ABSTRACT

A method for revealing the presence or absence of a particular microorganism strain in a culture medium, wherein at least two strain enzyme substrate chromogens are added to the culture medium, said chromogens being selected so that the presence of said strain in the culture medium is revealed by a third color.

14 Claims, No Drawings

METHOD FOR THE IDENTIFICATION OF MICROORGANISMS WITH AT LEAST TWO CHROMOGENS

The present invention relates to a method for demonstrating the presence or absence of a particular strain of microorganism in a culture medium.

The detection of microorganisms is very important, in particular in the food industry, in relation to water monitoring or in medicine, in view of the fact that these microorganisms may not only prove to be pathogenic agents, but can also consist of agents that reveal some types of contamination.

Various methods enable the presence of microorganisms in a medium of some kind to be demonstrated, consisting in taking a sample of the medium in question and then in promoting the growth of the microorganisms present by culture on or in a suitable medium.

In order to simplify the demonstration of the microorganisms present, the use has been proposed, in the detection medium, of colored compounds whose presence is characteristic of a given microorganism.

The coloration often reveals an enzyme activity associated with the microorganism in question, and the outcome of this activity may result in a modification of the pH of the medium, revealed by a colored indicator (EP-A-0 395 532), or alternatively in the liberation of a chromophoric or fluorophoric compound (FR-A-2-684,110).

Chromophores or fluorophores are compounds generally obtained by enzymatic hydrolysis of corresponding chromogenic or fluorogenic compounds present in the culture medium.

Fluorophores emit a characteristic radiation by fluorescence.

Chromophoric compounds are characterized by a color with a dominant wavelength.

Among known chromophoric compounds, indoxyl derivatives, hydroquinoline or alternatively naphthoic derivatives, or naphthyl and phenyl derivatives, may be noted in particular.

In order to differentiate two different genera of microorganisms in a culture medium, the proposal has even been made to introduce two chromogenic agents each liberating a chromophoric compound with a color characteristic of the presence of a particular microorganism (U.S. Pat. No. 5,210,022).

Although all of these media are efficacious in 10 detecting microorganisms of a specific genus, such as, for example, Salmonella, Candida or *E. coli*, and distinguishing them from other species, they do not, however, permit the detection of a large number of microorganisms of different genera on the same culture medium, or the differentiation of pathogenic species from others among microorganisms of the same genus.

Such a distinction appears to be all the more important for certain species of yeasts, such as *Candida albicans* which is responsible for more than 50% of pathologies associated with yeasts.

In point of fact, it was unexpectedly demonstrated that at least four different colorations enabling the strains to be characterized could be observed by introducing into the culture medium at least two chromogens which are substrates for enzymes of a particular strain, the two chromogens being chosen so that, in the culture medium, the presence of at least one strain is revealed by an accessory color, namely:

the two colors of the chromophores corresponding to the chosen chromogens, the color corresponding to the mixture of the chromophores, and the accessory color.

In many cases, the accessory color does not correspond to the mixture of the colors of the corresponding two chromophores, and is a color whose dominant wavelength does not correspond to the dominant wavelength of the mixture df chromophores liberated by the chromogens present in the culture medium, taken separately.

The dominant wavelength of the chromophores and the accessory colors may be calculated by reference to daylight, as defined by the CIE (International Commission on Energy as illuminant $D_{65}$, using any standard method for measuring the color of an object, especially with a spectrocolorimeter.

Hence the present invention relates to a method for demonstrating the presence or absence of a particular strain of microorganism in a culture medium, for which at least two chromogens which are enzyme substrates for said strain are introduced, said chromogens being chosen so that, in the culture medium, the presence of said strain is revealed by an accessory color.

The chromogens are, in particular, substrates for the following enzymes: β-galactosidase, β-glucosidase, β-glucuronidase, α-glucosidase, α-galactosidase, phosphatase, N-acetyl-β-glucosidase, N-acetyl-β-galactosidase, α-mannosidase, sulfatase, esterase, lipase and peptidase.

The chromogens are advantageously chosen from compounds of the same chemical family, preferably from those which liberate on hydrolysis two different chromophores which can undergo a coupling reaction.

Coupling reaction is understood to mean any physicochemical interaction through which the resulting dominant wavelength is different from the dominant wavelength of the mixture of the two chromophores taken separately.

Preferably, the chromogens are of the indoxyl family, especially alkylated, halogenated or dihalogenated indoxyl derivatives.

Preferred chromophores derived from indoxyl include the indoxyl derivatives bromoindoxyl, chloroindoxyl, dichloroindoxyl, chlorobromoindoxyl, trichloroindoxyl and methylindoxyl, especially the following derivatives: 6-chloroindoxyl, 5-bromoindoxyl, 3-bromoindoxyl, 4,6-dichloroindoxyl, 6,7-dichloroindoxyl, 5-bromo-4-chloroindoxyl, 5-bromo-6-chloroindoxyl or 4,6,7-trichloroindoxyl.

Microorganism whose presence or absence is demonstrated by the method according to the invention is understood to mean yeasts, molds or unicellular fungi and bacteria.

The method according to the invention is especially suitable for demonstrating the presence or absence of yeasts of the genus Candida, especially *Candida albicans* and *Candida tropicalis*.

Similarly, the bacteria whose presence or absence is capable of being demonstrated by the method according to the invention include, in particular, bacteria of the genus Streptococcus, Klebsiella, Enterobacter, Escherichia, Citrobacter, Staphylococcus, Listeria, Clostridium or Proteus.

Moreover, it was also found that the addition of a carbohydrate to the culture medium at a high concentration made it possible to increase the number of colors capable of being obtained by the method according to the invention, that is to say, for a limited number of chromogens, to obtain a high number of different colors enabling as many different microorganisms to be distinguished.

Consequently, the present invention relates to a method as defined above for which the culture medium possesses a high concentration of carbohydrate, prefeably glucose, in a peptone-based medium.

The high carbohydrate concentration is advantageously between 10 and 30 g/l.

Similarly, when at least one of the chromogens is a substrate for phosphatase, it is advantageous to employ a medium comprising a high phosphate concentration, preferably of between 1 and 3 g/l.

The examples recorded in the tables below enable the method according to the invention to be illustrated without, however, seeking to limit its scope.

TABLE I

Examples of single chromophores and of accessory colors
The following colors were observed for chromogens corresponding to different chromophores, and for mixtures in the same medium whose composition is as follows (g/l): agar (15), peptone (5), NaCl (5), yeast extract (2) and meat extract (1).

| Chromophore | Color |
| --- | --- |
| 5-bromo-4-chloro-3-indoxyl | bluish |
| 5-bromb-6-chloro-3-indoxyl | reddish |
| 6-chloro-3-indoxyl | pinkish |
| methylindoxyl | colorless |
| 5-bromo-4-chloro-3-indoxyl<br>5-bromo-6-chloro-3-indoxyl | metallic blue* |
| 5-bromo-4-chloro-3-indoxyl<br>6-chloro-3-indoxyl | metallic violet* |
| 6-chloro-3-indoxyl<br>methylindoxyl | purplish* |

*accessory color

TABLE II

Examples of coloration according to the invention for the direct identification of miscellaneous species of bacteria, also distinguishing *E. coli* from coliforms The media below one [sic] been prepared in a base, in g/l, agar (15), peptone (5), NaCl (5), yeast extract (2) and meat extract (1), with:
- A (mg/l): phenyl glucuronide (100), 5-bromo-4-chloro-3-indoxyl glucuronide (50), 5-bromo-6-chloro-3-indoxyl glucoside (50).
- B (mg/l): 5-bromo-4-chloro-3-indoxyl galactoside (50), 5-broxomo-6-chloro-3-indoxyl glucoside (50).
- C (g/l): 5-bromo-4-chloro-3-indoxyl glucoside (50), 6-chloro-3-indoxyl galactoside (50).

| | A | B | C |
| --- | --- | --- | --- |
| Streptococcus D | reddish | reddish | blue |
| Klebsiella | reddish | metallic blue* | metallic violet* |
| Enterobacter | reddish | metallic blue* | metallic violet* |
| Enterobacter MUG+ | metallic blue* | | |
| *E. coli* | blue | blue | pinkish |
| Citrobacter | reddish | metallic blue* | metallic violet* |
| *Proteus mirabilis* | colorless | colorless | colorless |

*accessory color

The colors given for the standard media are as follows:
Streptococcus D (blue), Klebsiella (blue), Enterobacter (blue), Enterobacter MUG+ (blue), *E. coli* (colorless), Citrobacter (colorless).

TABLE III

Examples of coloration according to the invention for miscellaneous species of yeast, demonstrating an accessory color and a coloration effect due to the presence of glucose and phosphate The media below were prepared:
- D (g/l): (comparative) agar (15), peptone (5), yeast extract (2), meat extract (1), NaCl (5), 5-bromo-4-chloro-3-indoxyl N-acetylglucosaminide (0.1).
- E (g/l): agar (15), peptone (10), glucose (20), phosphate (2), 5-bromo-4-chloro-3-indoxyl N-acetylglucosaminide (0.1), 5-bromo-6-chloro-3-indoxyl phosphate (0.1).

| | D | E |
| --- | --- | --- |
| *Candida albicans* | bluish | blue-green** |
| *Candida glabrata* | colorless | violet-pink** |
| *Candida guilliermondii* | | pale violet-pink** |
| *Candida krusei* | | violet-pink** |
| *Candida lusitaniae* | | pale violet-pink** |
| *Candida parapsilosis* | | gray-white** |
| *Candida tropicalis* | bluish | metallic blue* (with halo) |
| *Cryptococcus neoformans* | | pink-white** |
| *Trichosporon beigelii* | | gray-pink** |

*accessory color,
**medium effect

The above results show that the addition of glucose and phosphate makes it possible to broaden the range of colors available for the same medium, making it possible here to distinguish seven different species, and especially to identify *Candida albicans* unambiguously.

I claim:

1. A method for determining the presence or absence of a particular strain of microorganism in a culture medium, said method comprising:

introducing at least two chromogens which are enzyme substrates for said strain into said culture medium, said chromogens selected so that, in said culture medium, the presence of said strain is revealed by an accessory color, said accessory color having a dominant wavelength different than a dominant wavelength of the chromophore corresponding to each of the chromogens and different than a dominant wavelength of the mixture of the chromophore of each of the chromogens; and identifying the presence of said strain by identifying said accessory color.

2. The method of claim 1, wherein said chromogens are compounds of the same chemical family.

3. The method of claim 1 wherein said chromogens liberate on hydrolysis at least two different chromophores which undergo a coupling reaction to produce said accessory color.

4. The method of claim 1 wherein said chromogens are of the indoxyl family.

5. The method of claim 3, wherein said chromophore is selected from the indoxyl derivatives bromoindoxyl, chloroindoxyl, dichloroindoxyl, chlorobromoindoxyl, trichloroindoxyl and methylindoxyl.

6. The method of claim 1 wherein said microorganisms are yeasts.

7. The method of claim 6, wherein said yeasts are of the genus Candida.

8. The method of claim 1 wherein said microorganisms are bacteria.

9. The method of claim 8, wherein said bacteria are one of the genus Strertococcus, Klebsiella, Enterobacter, Escherichia, Citrobacter, Staphylococcus, Listeria, Clostridium and Proteus.

10. The method of claim 1, wherein said culture medium possesses a carbohydrate concentration in the range of 10 to 30 grams/liter.

11. The method of claim 10, wherein said carbohydrate concentration is a glucose concentration in a peptone-based medium.

12. The method of claim 1 wherein said chromogen is a substrate for phosphatase.

13. The method of claim 1, wherein said medium comprises a phosphate concentration in the range of 1 to 3 grams/liter.

14. The method of claim 3, wherein said chromophore is selected from the group consisting of 6-chloroindoxyl, 5-bromoindoxyl, 3-bromoindoxyl, 4,6-dichloroindoxyl, 6,7-dichloroindoxyl, 5-bromo-4-chloroindoxyl, 5-bromo-6-chloroindoxyl and 4,6,7-trichloroindoxyl.

* * * * *

UNITED STATES PATENT AND TRADEMARK OFFICE
CERTIFICATE OF CORRECTION

PATENT NO. : 5,962,251
DATED : October 5, 1999
INVENTOR(S) : Rambach It is certified that error appears in the above-identified patent and that said Letters Patent is hereby corrected as shown below:

In column 1, line 37, delete "hydroquinoline or alternatively" and insert -- hydroquinoline [sic] or alternatively -- .

In column 1, line 46, delete "efficacious in 10 detecting microorganisms" and insert -- efficacious in detecting microorganisms -- .

In column 2, line 10, delete "mixture df chromophores" and insert -- mixture of chromophores -- .

In column 2, line 14, delete "(International Commission on Energy" and insert -- (International Commission on Energy) -- .

In column 3, line 5, delete "prefeably glucose" and insert -- preferably glucose -- .

In column 3, line 26 (in Table I), delete "5-bromb-6-chloro-3-indoxyl" and insert -- 5-bromo-6-chloro-3-indoxyl -- .

UNITED STATES PATENT AND TRADEMARK OFFICE
CERTIFICATE OF CORRECTION

PATENT NO. : 5,962,251

DATED : October 5, 1999        PAGE 2 OF 2

INVENTOR(S) : Rambach

It is certified that error appears in the above-identified patent and that said Letters Patent is hereby corrected as shown below:

In column 3, line 48 (in Table II), delete "5-broxomo-6-chloro-3-indoxyl glucoside" and insert -- 5-bromo-6-chloro-3-indoxyl glucoside -- .

In column 5, line 8, delete "Strertococcus" and insert -- Streptococcus -- .

Signed and Sealed this

Twentieth Day of March, 2001

*Attest:*

NICHOLAS P. GODICI

*Attesting Officer*      *Acting Director of the United States Patent and Trademark Office*